United States Patent [19]

Kelman

[11] Patent Number: 4,469,097

[45] Date of Patent: Sep. 4, 1984

[54] MEDICAL BREATHING APPARATUS

[76] Inventor: Charles D. Kelman, 269-70 Grand Central Pkwy., Floral Park, N.Y. 11005

[21] Appl. No.: 381,919

[22] Filed: May 25, 1982

[51] Int. Cl.[3] .............................................. A61M 16/00

[52] U.S. Cl. ........................... 128/205.22; 128/205.24; 128/205.25; 128/207.12; 128/206.15; 128/206.19

[58] Field of Search ...................... 128/205.21, 205.22, 128/205.25, 201.23, 201.28, 206.28, 205.17, 207.18, 206.19, 910, 139, 200.27, 200.28, 204.26, 204.24, 205.24, 206.15, 207.12; 137/624.14

[56] References Cited

U.S. PATENT DOCUMENTS

| | | | |
|---|---|---|---|
| 1,221,446 | 4/1917 | Hecht | 128/139 |
| 2,038,310 | 4/1936 | Panettiere | 128/139 |
| 2,574,028 | 11/1951 | Fields et al. | 222/5 |
| 2,696,211 | 12/1954 | O'Gatty | 128/205 |
| 2,983,271 | 5/1961 | Beck | 128/146 |
| 3,130,722 | 4/1964 | Dempsey et al. | 128/206.28 |
| 3,276,445 | 10/1966 | Langdon | 128/146 |
| 3,438,370 | 4/1969 | Krantz, Jr. | 128/139 |
| 3,831,596 | 8/1974 | Cavallo | 128/204.23 |
| 3,867,936 | 2/1975 | Kelley | 128/910 |
| 3,991,753 | 11/1976 | Viesca y Viesca | 128/139 |
| 4,019,508 | 4/1977 | Der Estephinian et al. | 128/139 |
| 4,296,746 | 10/1981 | Mason, Jr. et al. | 128/201.15 |
| 4,323,063 | 4/1982 | Fisichella | 128/139 |
| 4,381,002 | 4/1985 | Mon | 128/204.24 |
| 4,440,162 | 4/1984 | Spergel | 128/205.22 |

FOREIGN PATENT DOCUMENTS

| | | | |
|---|---|---|---|
| 902715 | 12/1953 | Fed. Rep. of Germany | 128/139 |
| 768083 | 5/1934 | France | 128/205.22 |

*Primary Examiner*—Henry J. Recla
*Assistant Examiner*—Karin M. Reichle
*Attorney, Agent, or Firm*—Henry Sternberg

[57] ABSTRACT

Medical breathing apparatus which provides repeated short bursts of oxygen separated by longer intervals of time to the wearer of a surgical mask to supplement his breathing.

8 Claims, 2 Drawing Figures

MEDICAL BREATHING APPARATUS

Figure 1:
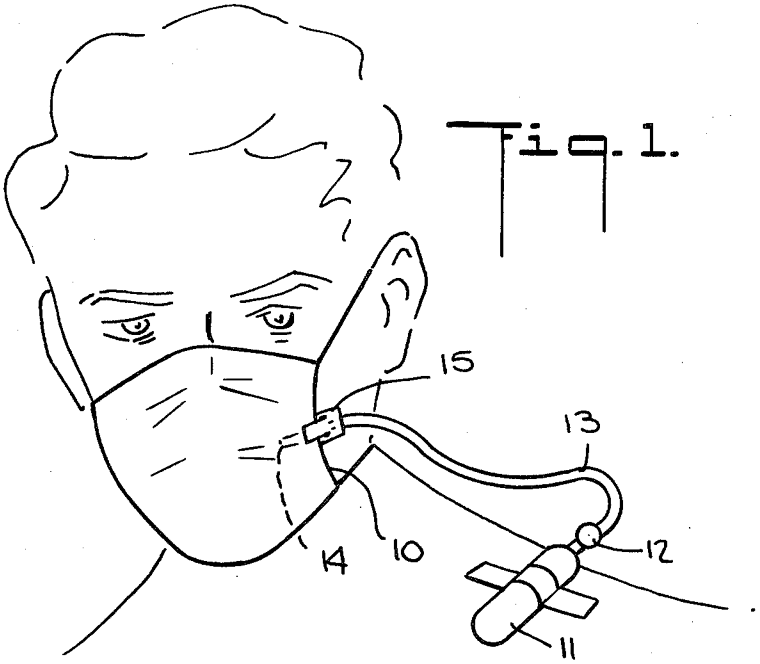

This invention relates to medical breathing apparatus and, more particularly, to such apparatus which is mobile and may be worn by a surgeon.

During extremely delicate surgical operations extending over a long period of time, for example, an hour or more, the usual gauze surgical masks used by the surgeon causes carbon dioxide exhaled by the surgeon to build up within the mask and between the surgeon's face and the mask and to be inhaled again. Over a long period of time this can cause the surgeon to develop a headache and otherwise impair his faculties. To relieve this condition, some surgeons lower the mask below the nose so that they can inhale freely. This practice is, of course, undesirable since it risks exposing the patient to air exhaled by the surgeon.

U.S. Pat. No. 4,296,746 discloses a disposable full-face surgical mask which can be used with an air compressor strapped to the body of the wearer for supplying air to an air intake filter vent in the mask. Such an air compressor is larger and heavier than is desirable for a surgeon to wear.

It is an object of the present invention, therefore, to provide a new and improved breathing apparatus which avoids one or more limitations of prior such apparatus.

It is another object of the invention to provide new and improved medical breathing apparatus which is mobile and of small size and weight and may be worn by a surgeon, providing minimum interference with an operation performed by him.

In accordance with the invention, medical breathing apparatus comprises a surgical mask and a container for pressurized gas. The apparatus also includes means for coupling the surgical mask to the container and valve means operable to be open for repeated short intervals of time separated by longer intervals of time for dispensing gas in bursts from the container to the surgical mask.

For a better understanding of the present invention, together with other and further objects thereof reference is made to the following description, taken in connection with the accompanying drawings, and its scope will be pointed out in the appended claims.

Figure 2:
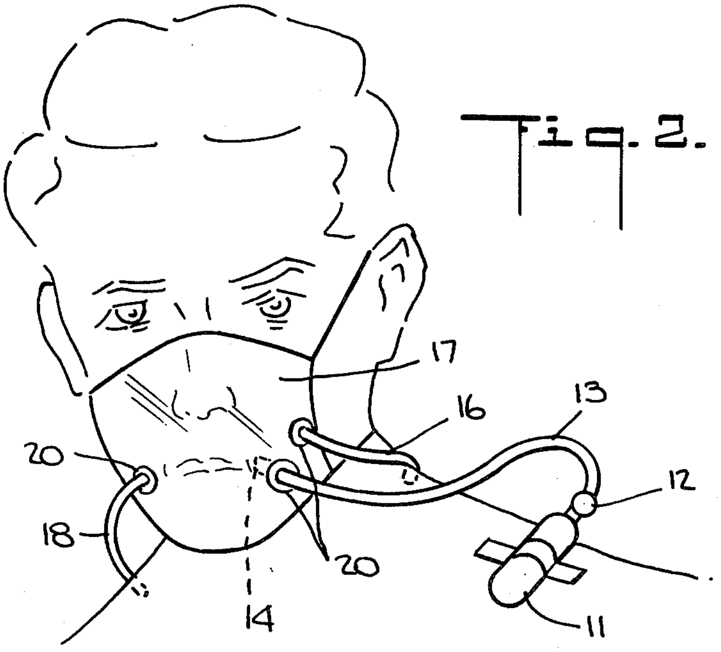

Referring now to the drawings:

FIG. 1 is a schematic view of medical breathing apparatus constructed in accordance with the invention for use by a surgeon; and FIG. 2 is a schematic view of another embodiment of medical breathing apparatus constructed in accordance with the invention for use by a surgeon.

Referring now more particularly to FIG. 1 of the drawing, there is represented medical breathing apparatus constructed in accordance with the invention. The apparatus comprises a surgical mask 10, which may be of a conventional gauze type. The apparatus also includes a container 11 for pressurized gas, more particularly a mobile container for pressurized oxygen. The container 11 may, for example, be a cylindrical metal container a few inches long and between ½ to one inch in diameter which may be attached to the gown of a surgeon without impairing his ability to move.

The apparatus also includes means for coupling the surgical mask 10 to the container 11 and valve means 12 operable to be open for repeated short intervals of time separated by longer intervals of time for dispensing gas in bursts from the container to the surgical mask. The coupling means includes, for example, plastic tubing 13 connecting the valve means 12 to the mask 10 with its outlet 14 attached by a clip 15 to the mask 10 between the mask 10 and the face of the surgeon.

The valve means 12 may be directly connected to the outlet of the container 11 and preferably is a pressure-actuated valve which automatically opens periodically for a short period of time, for example, approximately one second and remains closed during intervening intervals of, for example, approximately twenty seconds. Such a valve may, for example, be of the type described in U.S. Pat. No. 3,826,280. Alternatively, the valve may, for example, be inside the container.

Alternatively, the valve 12 may be a conventional solenoid valve controlled for periodic opening by a suitable timer.

Accordingly, the FIG. 1 breathing apparatus is effective to supply oxygen or air, in short bursts or spurts, spaced periodically, to supplement the breathing of the surgeon through the material of the mask 10. Because the oxygen is supplied in short bursts separated by much longer intervals, the container for the oxygen may be sufficiently small and lightweight as not to impede the surgeon.

Referring now more particularly to FIG. 2 of the drawings, the apparatus there represented includes a transparent preferably rigid plastic surgical mask of, for example, polyethylene. Such a mask has as an advantage that the face of the surgeon is visible to other members of the surgical team and furthermore may be photographed while the surgeon is wearing the mask.

An air-inlet tube 16 which may be of suitable plastic material is attached to the mask 17 preferably at one side thereof, to provide an air inlet through the mask from a suitable location, for example, behind the surgeon, to the space between the mask 17 and the face of the surgeon.

An air-outlet tube 18 which may be of suitable plastic material is attached to the mask 17 at preferably the other side thereof, to provide an outlet through the mask from the face of the surgeon to a suitable location, for example, behind the surgeon. The air inlet as well as the air outlet tube may be connected to the rigid mask 17 by suitable grommets 20 or the like, so that they pass through the mask. Alternatively, the mask 17 could, for example, have plastic nipples to which tubes are connected.

The FIG. 2 apparatus also includes a container 11 and a valve 12 similar to the corresponding container and valve of the FIG. 1 embodiment. In this case, however, the tube 13 may be connected to and pass through the mask by a grommet 20.

While there have been described what are at present considered to be the preferred embodiments of this invention, it will be obvious to those skilled in the art that various changes and modifications may be made therein without departing from the invention, and it is, therefore, aimed to cover all such changes and modification as fall within the true spirit and scope of the invention.

What is claimed is:

1. Medical breathing apparatus comprising:
a surgical mask;
a container for pressurized gas;
means for coupling said surgical mask to said container; and
valve means automatically opened periodically by the pressurized gas in said container for repeated short intervals of time separated by longer intervals of time for dispensing gas in bursts from said container to said surgical mask, whereby said short and longer intervals of time are determined by said valve means independently of the breathing cycle of the wearer of the mask.

2. Apparatus in accordance with claim 1 in which said container is a mobile container which may be worn by a surgeon.

3. Apparatus in accordance with claim 1 in which said surgical mask is primarily of a transparent plastic material.

4. Apparatus in accordance with claim 3 in which said mask is rigid and which further comprises air inlet and outlet means for admitting and expelling, respectively, from and to a region away from the operating field, the air breathed by the surgeon.

5. Apparatus in accordance with claim 1 in which said gas is oxygen.

6. Apparatus in accordance with claim 1 which includes means for supporting the container on a surgeon's body.

7. Apparatus in accordance with claim 1 in which said valve means is operable to be open for repeated short intervals of approximately one second separated by longer intervals of approximately twenty seconds.

8. Medical breathing apparatus comprising:

a surgical gauze mask;

a container for pressurized gas;

means for coupling said surgical mask to said container; and valve means operable to be open for repeated short intervals of time separated by longer intervals of time for dispensing gas in bursts from said container to said surgical mask, said short and longer intervals of time being determined by said valve means independently of the breathing cycle of the wearer of the mask.

* * * * *